US00PP16656P2

(12) United States Plant Patent
Huisman

(10) Patent No.: US PP16,656 P2
(45) Date of Patent: Jun. 13, 2006

(54) ***CAMPSIS* PLANT NAMED 'HUITAN'**

(50) Latin Name: *Campsis radicans*
Varietal Denomination: Huitan

(76) Inventor: Marinus Huisman, Veldlaan 70, Boskoop (NL), 2771 LZ ( * ) Notice: Subject to any disclaimer, the term of this patent is extended or adjusted under 35 U.S.C. 154(b) by 94 days.

(21) Appl. No.: 10/862,144

(22) Filed: Jun. 7, 2004

(51) Int. Cl.
*A01H 5/00* (2006.01)

(52) U.S. Cl. ..... Plt./226
(58) Field of Classification Search ..... Plt./226
See application file for complete search history.

(56) References Cited

U.S. PATENT DOCUMENTS

PP4,119 P * 10/1977 Flemer, III ..... Plt./226
PP12,245 P2 * 12/2001 Wakaiki ..... Plt./226
PP13,139 P2 * 10/2002 Kuijf ..... Plt./226

OTHER PUBLICATIONS

UPOV ROM GTITM Computer Database, GTI Jouve Retrieval Software 2005/02 Citation for 'Huitan'.*

* cited by examiner

*Primary Examiner*—Kent Bell
*Assistant Examiner*—W. C. Haas

(57) ABSTRACT

A new and distinct cultivar of *Campsis* named 'Huitan' that is characterized by upright compact habit, glossy green leaves, and many coral-red flowers to a flowering stem. In combination these traits set 'Huitan' apart from all other existing varieties of *Campsis* known to the inventor.

2 Drawing Sheets

Botanical designation: *Campsis radicans.*
Variety denomination: 'Huitan'.

BACKGROUND OF THE INVENTION

The present invention relates to a new and distinct cultivar of trumpet creeper that is grown for use as an ornamental landscape plant. The new cultivar is known botanically as *Campsis radicans* and will be referred to hereinafter by the cultivar name 'Huitan'.

The inventor selected 'Huitan' in 1996 as an individual plant found growing amongst a batch of plants at the inventor's nursery in Boskoop, The Netherlands. The inventor has been interested in the genus *Campsis* and maintains a collection of named cultivars and unnamed selections which have arisen at the inventor's nursery through open pollination.

The batch of plants from which the inventor selected 'Huitan' was raised by the inventor from seed which the inventor collected from a plant of *Campsis radicans* 'Flamenco' (unpatented). This plant had been open-pollinated and the pollen parent was an unknown and unnamed selection of *Campsis radicans.*

The new *Campsis* plant 'Huitan' is a semi-evergreen flowering vine suitable for use in containers, against walls, trellis, or other structures in the landscape. Cultural requirements include all soil types, light shade or full sun, and regular water. The distinguishing characteristics of the new cultivar 'Huitan', are shiny dark-green leaves, many coral-red flowers per shoot, and compact upright habit.

The closest named comparison plant known to the inventor is the seed or female parent *Campsis radicans* 'Flamenco'. In general, plants of *Campsis radicans* are robust and vigorous climbers, with variability in flower coloration between yellow-orange and red and typically achieving heights of at least 10 meters. *Campsis radicans* 'Flamenco' achieves this height also but was selected for the clarity of its orange red flowers. The flowers of 'Huitan' are clear red in color and the plant habit of 'Huitan' is much more compact. After three season's growth, the height of 'Huitan' is approximately 3 meters.

'Huitan' was first asexually propagated by the inventor in 1996 in a cultivated area of Boskoop, The Netherlands. The method of propagation used was vegetative cuttings. Since that time in successive generations of asexual reproduction, 'Huitan' has remained stable, uniform and true to type.

SUMMARY OF THE INVENTION

The following represent the distinguishing characteristics of the new *Campsis* cultivar 'Huitan'. In combination these traits set 'Huitan' apart from all other existing varieties of *Campsis* known to the inventor. 'Huitan' has not been tested under all possible conditions and phenotypic differences may be observed with variations in environmental, climatic, and cultural conditions, however, without any variance in genotype.

1. *Campsis* 'Huitan' is a perennial that blooms midsummer to fall.
2. *Campsis* 'Huitan' exhibits an upright compact habit.
3. *Campsis* 'Huitan' exhibits many flowers per flowering stem.
4. *Campsis* 'Huitan' produces red trumpet-shaped flowers.
5. *Campsis* 'Huitan' exhibits glossy dark-green leaves.
6. *Campsis* 'Huitan' is a semi-evergreen vine.
7. *Campsis* 'Huitan' is 35 cm. in diameter and 65 cm. in height after one growing season and approximately 3 m in height at maturity.
8. *Campsis* 'Huitan' is hardy to USDA Zone 7.
9. *Campsis* 'Huitan' is an ornamental landscape plant suitable for use on trellis, wall, or as a screen in the landscape.

BRIEF DESCRIPTION OF THE DRAWINGS

The accompanying color drawings illustrate the overall appearance of the new *Campsis* variety 'Huitan' showing the colors as true as it is reasonably possible to obtain in colored reproductions of this type. Colors in the drawings may differ from the color values cited in the detailed botanical description, which accurately describe the actual colors of the new variety 'Huitan'.

The drawing labeled as FIG. 1 illustrates an entire two-year-old plant in flower which has been grown out-of-doors in a 1-liter container.

Figure 1:
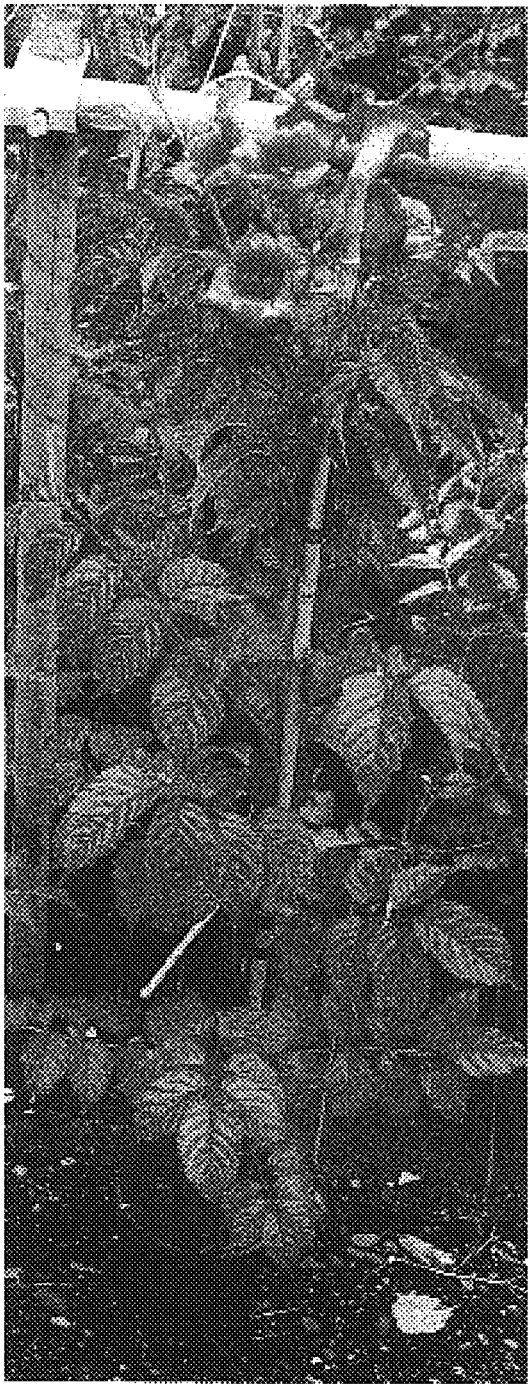
Figure 2:
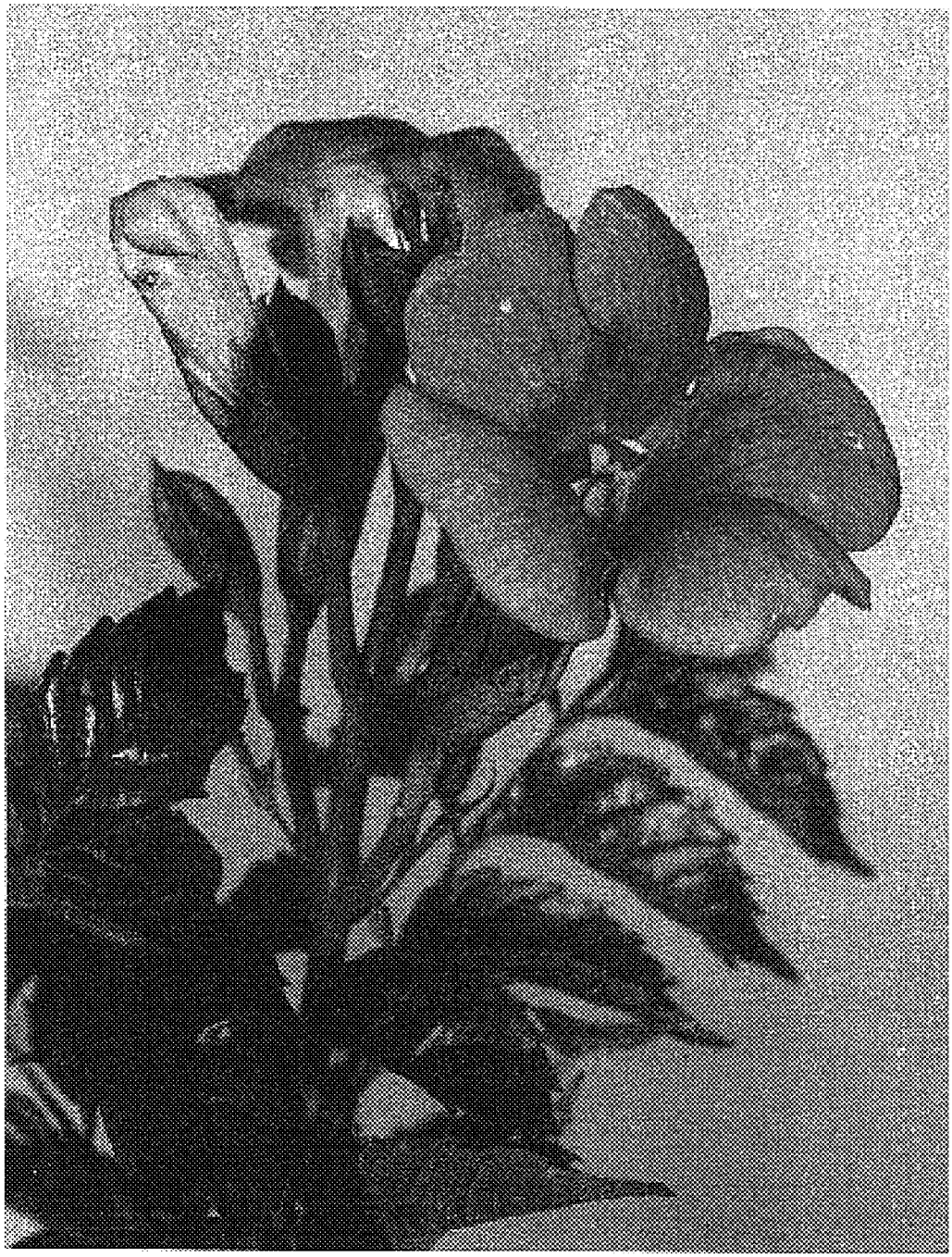

The drawing labeled as FIG. 2 illustrates a close-up view of the flowers.

The drawings were made using conventional techniques and although colors may appear different from actual colors due to light reflectance, they are as accurate as possible by conventional photography.

BOTANICAL DESCRIPTION OF THE PLANT

The following is a detailed description of the *Campsis* cultivar named 'Huitan'. Data was collected by the inventor in Boskoop, The Netherlands from 12-month-old plants, in September, that were grown out-of-doors in 1-liter containers. The average daytime temperatures were 14° C. to 28° C. with normal outdoor light level, and the average nighttime temperatures were 7° C. to 16° C. Color determinations are in accordance with The 2001 Royal Horticultural Society Colour Chart except where general color terms of ordinary dictionary significance are used. The growing requirements are similar to the species and there are no disease problems known to the inventor. No growth retardants or photoperiodic treatments were applied to the plants.

Botanical classification: *Campsis radicans* 'Huitan'.
Species: *Radicans*.
Common name: Trumpet creeper.
Commercial classification: Vine.
Type: Perennial.
Use: Used as an ornamental for container, trellis, wall, or other structures in the landscape.
Parentage: Open pollinated plants of *Campsis radicans*.
Growth habit: Upright climbing habit.
Growth rate: Grows 20 cm. per month in spring.
Plant height: 65 cm. after one growing season and approximately 3 m in height after three growing seasons.
Plant width: 35 cm. in width.
Vigor: Moderate.
Hardiness: USDA Zone 7.
High temperature tolerance: At least up to 35° Centigrade.
Recommended crop container size: 14 cm. pots.
Propagation: Vegetative cuttings.
Root system: Both underground and aerial roots as later described. Cultural requirements: Plant in full sun or partial shade, and well-drained soil with regular to moderate water.
Seasonal interest: Coral-red flowers from midsummer to fall.
Time to develop to commercial container size: An average of 6 months are needed to produce a 14-cm container plant from a cutting.
Special growing requirements or growing problems: None known to the inventor.
Disease and pest susceptibility: No susceptibility to disease and pests known to the inventor.
Stem:
- *Branching habit.*—Compact basal branching and lateral branching.
- *Stem diameter.*—6 mm. in diameter.
- *Stem length.*—55 cm. in length.
- *Stem strength.*—Strong.
- *Stem shape.*—Cylindrical.
- *Internode length.*—6.4 cm. between nodes.
- *Stem surfaces.*—Glabrous.
- *Pubescence.*—None observed.
- *Stem color.*—A combination of 143A and 143B is present on an individual stem. Individual colors N199A and N199B are present on older bark at the stem base.
- *Lenticels.*—Present.
- *Lenticel shape.*—Lens-shaped.
- *Quantity of lenticels.*—Average of 15 per cubic centimeter.
- *Length of lenticel.*—0.75 mm in length.
- *Width of lenticel.*—0.4 mm. in width.
- *Lenticel color.*—161A.

Aerial roots:
- *Length* (*average*).—4 mm.
- *Diameter.*—1 mm.
- *Texture and surface.*—Fleshy, smooth.
- *Color.*—Ranges between 199B and 199C.

Underground roots: Thick, fleshy, sparse with little lateral branching.
- *Color.*—Ranges from light gray brown 199D to gray-green 196C.

Foliage:
- *Type.*—Semi-evergreen.
- *Leaf arrangement.*—Opposite.
- *Leaf division.*—Compound.
- *Leaf shape.*—Pinnate.
- *Leaves per lateral branch.*—Average number of 16 leaves or 8 pairs.
- *Quantity of leaflets per leaf.*—A range of 7–9 leaflets per leaf.
- *Leaflet margin.*—Entire.
- *Leaflet shape.*—Ovate.
- *Leaflet apex.*—Apiculate.
- *Leaflet base.*—Attenuate.
- *Leaflet length.*—Leaflet length ranges from 6.6 cm. to 7.2 cm. in length.
- *Leaflet width.*—Leaflet width ranges from 3.3 cm. to 3.5 cm. in width.
- *Leaflet surface* (*adaxial and abaxial surfaces*).—Most glabrous with only a Few hairs along veins on abaxial surface.
- *Leaflet appearance.*—Glossy.
- *Leaflet margin.*—Serrate.
- *Venation pattern.*—Pinnate.
- *Vein color* (*adaxial surface*).—138B.
- *Vein color* (*abaxial surface*).—138C.
- *Young leaflet color* (*adaxial surface*).—137B.
- *Young leaflet color* (*abaxial surface*).—137D.
- *Mature leaflet color* (*adaxial surface*).—139A.
- *Mature leaflet color* (*abaxial surface*).—137C.
- *Leaf attachment.*—Rachis.
- *Rachis length.*—Average is 14.3 cm. in length.
- *Rachis diameter.*—Average is 3 mm. in diameter.
- *Rachis color.*—143A.
- *Rachis durability.*—High durability to stress.
- *Petioles.*—Absent.
- *Stipules.*—Tendrils, thorns: Absent.

Flower:
- *Flower arrangement.*—Terminal thyrse.
- *Type of inflorescence.*—Thyrse.
- *Inflorescence height.*—16 cm. in height.
- *Inflorescence width.*—17 cm. in width.

*Quantity of flowers per inflorescence.*—An average of 38 flowers per inflorescence.
*Shape of flower.*—Trumpet-shaped.
*Blooming period.*—Blooms continuously from late July to September.
*Quantity of buds per flowering stem.*—An average of 38 buds per flowering stem.
*Quantity of buds and flowers per plant.*—An average of 76 buds and flowers per plant.
*Natural flowering season.*—Summer.
*Response time.*—Approximately 9 months for field grown plant to flower.
*Rate of flower opening.*—Approximately 10% of the flowers are open at any stage.
*Fragrance.*—None observed.
*Flower bud length.*—3 cm. in length.
*Flower bud diameter.*—1.2 cm. in diameter.
*Flower bud shape.*—Obovate.
*Flower bud apex.*—Apiculate.
*Flower bud color.*—Individual colors 152B, 153A, and 153B are present on an individual bud.
*Flower aspect.*—Facing outward and upward.
*Dimensions of flower.*—6.4 cm. in diameter and 7.1 cm. in height.
*Lastingness of flower on plant.*—Approximately 5 days.
*Persistent or self-cleaning.*—Self-cleaning.
*Petal surface* (*adaxial and abaxial surface*).—Glabrous.
*Petal appearance* (*adaxial and abaxial surface*).—Matte appearance.
*Petals.*—5 in number.
*Fused or unfused.*—Petal basally fused.
*Petal shape.*—Flabellate.
*Petal margin.*—Entire.
*Petal apex.*—Retuse.
*Petal length.*—Average of 6.9 cm. in length.
*Petal width.*—Average of 3.4 cm. in width.
*Petal color when opening* (*adaxial surface*).—Colors 43A, 43B 30A, and 30B are all individually present on an individual petal.
*Petal color when opening* (*abaxial surface*).—Colors 32A, 32B, 33A, and 33B are individually present on an individual petal.
*Petal color when fully opened* (*adaxial surface*).—Individual colors 46B and 33A are present on an individual petal.
*Petal color when fully opened* (*abaxial surface*).—Individual colors 33B and 33A are present on an individual petal.
*Fading petal color.*—No fading observed in flower color.
*Calyx dimensions.*—3.5 cm. in length and 1.5 cm. in width.
*Calyx shape.*—Campanulate.
*Calyx surface.*—Glabrous.
*Sepals fused or unfused.*—Fused.
*Number of sepals.*—Five sepals.
*Sepal color* (*adaxial and abaxial surfaces*).—N189C.
*Sepal surfaces* (*adaxial and abaxial surfaces*).—Glabrous.
*Sepal dimensions.*—Averages of 3.5 cm. in length and 7 mm. in width.
*Sepal margin.*—Entire.
*Sepal shape.*—Narrow elliptic.
*Sepal apex.*—Acuminate.
*Sepal color* (*adaxial surface*).—Individual colors152B 153A 153B. 167A, and 153B are present on an individual plant.
*Sepal color* (*abaxial surface*).—Individual colors 152B, 153A, 153B, 26B, and 26C are present on an individual plant.
*Pedicel dimensions.*—Average dimensions of pedicel 1.1 cm. in length and 3 mm. in width.
*Pedicel surface.*—Glabrous.
*Pedicel strength.*—Strong.
*Pedicel angle.*—Average angle is 0° to 30°.
*Pedicel color.*—N144A.
*Peduncle length.*—Average of 15 cm. in length.
*Peduncle diameter.*—Average of 3 mm. in diameter.
*Peduncle angle.*—Straight upright, 0° angle.
*Peduncle strength.*—Strong.
*Peduncle color.*—A combination of colors143A and 143B are present on an individual peduncle.
*Flower fragrance.*—None observed.

Reproductive organs:
*Stamens.*—4 in number.
*Stamen shape.*—Filament.
*Stamen color.*—155A.
*Stamen length.*—2.7 mm. in length.
*Anther shape.*—Sagittate.
*Anther color.*—11B.
*Anther dimensions.*—3 mm. in length and 1.25 mm. in width.
*Pollen amount.*—Low amount.
*Pollen color.*—8A.
*Number of pistils.*—1 in number.
*Pistil shape.*—Filament.
*Pistil length.*—4.3 cm. in length.
*Stigma shape.*—Flattened ovate.
*Stigma color.*—152C.
*Style length.*—4 cm. in length.
*Style color.*—153B.
*Ovary.*—Present.
*Ovary color.*—144C.

Seed: No seed production has been observed to date.

What is claimed is:

1. A new and distinct variety of *Campsis* plant named 'Huitan' as described and illustrated herein.

* * * * *